US012576152B2

(12) United States Patent
James et al.

(10) Patent No.: US 12,576,152 B2
(45) Date of Patent: *Mar. 17, 2026

(54) TOPICAL COMPOSITION

(71) Applicant: Futura Medical Developments Limited, Guildford (GB)

(72) Inventors: Kenneth William James, Guildford (GB); James Andrew Provost, Guildford (GB)

(73) Assignee: FUTURA MEDICAL DEVELOPMENTS LIMITED, Guildford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/252,084

(22) Filed: Jun. 27, 2025

(65) Prior Publication Data

US 2025/0352650 A1     Nov. 20, 2025

Related U.S. Application Data

(63) Continuation of application No. 17/783,873, filed as application No. PCT/GB2020/052660 on Oct. 22, 2020, now Pat. No. 12,414,992.

(30) Foreign Application Priority Data

Dec. 9, 2019     (GB) ..................................... 1918039
Sep. 29, 2020     (GB) ..................................... 2015404

(51) Int. Cl.
| | |
|---|---|
| *A61K 47/10* | (2017.01) |
| *A61K 9/00* | (2006.01) |
| *A61K 31/417* | (2006.01) |
| *A61K 31/5575* | (2006.01) |
| *A61K 45/06* | (2006.01) |
| *A61L 31/14* | (2006.01) |

| | |
|---|---|
| *A61P 15/10* | (2006.01) |
| *G01N 25/48* | (2006.01) |

(52) U.S. Cl.
CPC ............ *A61K 47/10* (2013.01); *A61K 9/0014* (2013.01); *A61K 9/0034* (2013.01); *A61K 31/417* (2013.01); *A61K 31/5575* (2013.01); *A61K 45/06* (2013.01); *A61L 31/14* (2013.01); *A61P 15/10* (2018.01); *G01N 25/4846* (2013.01)

(58) Field of Classification Search
CPC ...... A61P 15/10; A61L 31/14; G01N 25/4846
See application file for complete search history.

(56) References Cited

U.S. PATENT DOCUMENTS

| | | | | |
|---|---|---|---|---|
| 5,093,133 A * | 3/1992 | Wisniewski | ......... | A61K 9/0014 424/444 |
| 6,183,766 B1 * | 2/2001 | Sine | ......... | A61P 17/00 424/404 |
| 6,333,039 B1 * | 12/2001 | Fendler | ......... | A61K 8/8117 424/420 |
| 2019/0365732 A1 * | 12/2019 | Ritter | ......... | A61K 47/10 |

* cited by examiner

*Primary Examiner* — Jared Barsky
(74) *Attorney, Agent, or Firm* — Stites & Harbison, PLLC; Terry L. Wright

(57) ABSTRACT

There is provided a composition for topical application to the penis for the treatment of erectile dysfunction, the composition being free of glyceryl trinitrate (GTN), sildenafil and an acetylcholinesterase inhibitor, and comprising volatile and non-volatile solvents, the volatile solvents comprising a lower alcohol and water and the non-volatile solvents comprising a polyhydric alcohol and a glycol. Preferably, the composition does not contain any pharmaceutically active ingredients for the treatment of erectile dysfunction. Also provided is a method of determining the cooling ability of a test composition, such as the composition described above.

11 Claims, 3 Drawing Sheets

Average Temperature (°C) of Sample Gel over Time (min) at each ambient temperature (27°C, 32°C, 37°C)

TOPICAL COMPOSITION

RELATED APPLICATIONS

This application is a continuation application of U.S. application Ser. No. 17/783,873, filed Jun. 9, 2022, and which is a $371 national stage application of International Patent Application No. PCT/GB2020/052660, filed Oct. 22, 2020, which claims priority to United Kingdom Patent Application Nos. 1918039.7, filed Dec. 9, 2019, and 2015404.3, filed Sep. 29, 2020, the entire disclosures of which are incorporated herein by this reference.

FIELD OF THE INVENTION

This invention relates to compositions for the treatment or amelioration of conditions susceptible to vascular smooth muscle relaxation, especially erectile dysfunction.

BACKGROUND TO THE INVENTION

WO 2019/034878, in the name of the present Applicant—Futura Medical Developments Ltd, includes a comprehensive review of, and patent and non-patent literature relating to, erectile dysfunction and previous attempts to provide a solution thereto. In particular, it describes and claims a composition for topical application especially to the glans of the penis, the composition comprising glyceryl trinitrate (GTN) as active ingredient dissolved in a blend of volatile and non-volatile solvents of different solvating capacities for the GTN, in which the volatile solvents comprise water and a lower alcohol and the non-volatile solvents comprise a polyhydric alcohol and a glycol. The polyhydric alcohol and the glycol are required to have a ratio by weight of from 1.5:1 to 6.0:1 and the composition is required to have a pH in the range 5.1-7.0.

The role of compositions as described in WO 2019/034878 is to provide rapid initial absorption of GTN and an ongoing slow absorption as the volatile solvents evaporate in use so that the GTN concentration is dynamically maintained even as depletion through absorption takes place. The GTN promotes the formation of exogenous nitric oxide (NO) in the penile cavernosa to supplement the endogenous NO synthesised internally following stimulation of the glans by manual application of the composition, thus resulting in tumescence and a firm and self-sustaining erection. (See "Development of a novel topical formulation of glyceryl trinitrate for the treatment of erectile dysfunction", Davis, Adrian and Reisman, Yacov, accepted for publication in IJIR: Your Sexual Medicine Journal, Nov. 27, 2019).

Clinical trial results for the compositions of WO 2019/034878 are highly encouraging: the compositions have been shown as providing statistically significant improvements with the three primary end points (IIEF, SEP2 AND SEP3) compared with baseline data with over 60% of all subjects experiencing a meaningful difference in improvement of their erections using industry-standard assessment techniques. Over 60% of subjects saw a speed of onset of within ten minutes of application, significantly faster than sildenafil with resulting significant benefits in spontaneity. Furthermore, no serious side effects were reported by any subjects and there was a highly favourable overall side effect profile across all doses.

Despite the favourable side effect profile overall, there remain some minor disadvantages which it would be preferable to eliminate. For example, headache is experienced by a small number of users and, while not being a serious side effect in itself, it is undeniably a problem in the circumstances of use. More significantly, the use of compositions containing GTN is contra-indicated for men having medical conditions for which they take nitrate-containing medication. There is thus, despite the clinical success of GTN-containing compositions as disclosed in WO 2019/034878, an ongoing need to provide an effective formulation which does not contain GTN. There is in any event a general desire to provide compositions which do not contain synthetic chemicals as active ingredients, in alignment with the current trend towards the preferred use of "natural" remedies.

WO 2010/044094 describes a topical composition for treatment of erectile dysfunction and pulmonary hypertension, comprising sildenafil citrate, lidocaine and pharmaceutically acceptable excipients. In contrast, the composition of the present invention is free of sildenafil and lidocaine.

US 2014/0227342 describes a composition comprising an acetylcholinesterase inhibitor, a solvent and a permeation enhancer in a pharmaceutically acceptable carrier. In contrast, the composition of the present invention is free of an acetylcholinesterase inhibitor.

SUMMARY OF THE INVENTION

It has been unexpectedly found that the blend of excipients described in WO 2019/034878, without addition of GTN and when used as a treatment for erectile dysfunction, provides results which demonstrate that their efficacy is comparable with the GTN-containing equivalent composition.

In one aspect, the present invention provides a composition for topical application to the penis for the treatment of erectile dysfunction, the composition being free of GTN and comprising volatile and non-volatile solvents, the volatile solvents comprising a lower alcohol and water and the non-volatile solvents comprising a polyhydric alcohol and a glycol.

The polyhydric alcohol and glycol preferably have a ratio by weight of from 1.5:1 to 6.0:1. Preferably, the pH of the composition is above 5.0 and lower than 7.0.

Speculatively, compositions according to the invention, while being unable (due to the absence of active ingredient) to stimulate production of exogenous NO, nevertheless enhance production of endogenous NO by virtue, for example, of the latent heat of cooling as the volatile solvent component evaporates, stimulating the nerves locally and resulting in generation of endogenous NO. In organs or parts thereof which are very highly enervated, therefore, such as the glans of the penis, there are sensors which are reactive to a range of physical sensations, such as and including touch, pressure and temperature, and topical application to such organs of compositions according to invention may stimulate more than one such sensor so that they react synergistically and, in the case of the penis, results in tumescence and erection without the inclusion of an active ingredient as such, whereas topical application of, for example, a known gel formulation containing sildenafil or of a personal lubricant has been found to have no effect on erectile capability.

The composition is free of GTN, i.e. it does not contain any GTN. Further, the composition preferably does not contain any derivatives or prodrugs of GTN.

Preferably, the composition is also free of sildenafil and an acetylcholinesterase inhibitor. "Sildenafil" also encompasses salt forms, such as sildenafil citrate. The acetylcholinesterase inhibitor may be any acetylcholinesterase inhibitor such as Δ9-tetrahydrocannabinol (THC), physostigmine, neostigmine, pyridostigmine, ambenonium, demarcarium, rivastigmine, galantamine, caffeine, donepezil, tetrahydroaminoacridine, edrophonium, huperzine A, bis-huperzine A, bis-huperzine B, huperzine A-tacrine, derivatives of huperzine A, ladostigil, ungeremine, and lactucopicrin.

The composition may also be free of lidocaine. The term "lidocaine" also encompasses salt forms, such as its hydrochloride salt.

In some embodiments, the composition does not contain any pharmaceutically active ingredients for the treatment of erectile dysfunction, for example, phosphodiesterase type 5 inhibitors (PDE5 inhibitors) such as tadalafil and sildenafil, and vasodilators such as alprostadil and phentolamine mesilate. In some embodiments, the composition does not contain any pharmaceutically active ingredients.

In some embodiments, the composition is free of compounds selected from PDE-5 inhibitors, amide anaesthetics, local anaesthetics, natural prostaglandins, synthetic prostaglandins, testosterone or combinations thereof. Preferably, the composition is free of PDE-5 inhibitors and amide anaesthetics.

In particular embodiments, the composition does not comprise white petroleum jelly and/or paraffin.

The composition is not intended for use as a hand sanitizer. The composition may have a lower alcohol content of not more than 50%, optionally not more than 45%, optionally not more than 40%, further optionally not more than 36%. In some embodiments, the composition has an ethanol content of not more than 50%, optionally not more than 45%, optionally not more than 40%, further optionally not more than 36%.

Preferably the composition is in gel, cream or serum form although other forms, such as foams or sprays, may be contemplated and are within the scope of the invention with appropriate additive excipients, for example a propellant gas in the case of a foam or spray. More preferably, the formulation is a gel. In formulation types where the composition has the form of a gel and is applied by hand, viscosities in the range of 125,000-600,000 mPas are appropriate to ensure optimum control of application, as governed by the pH being in the range 5.0-7.0. Preferably, the viscosity should have a value in the range 200,000 to 450,000 mPas, more preferably 250,000-350,000 mPas, for example 300,000 mPas when measured by Brookfield Viscometer, Spindle E, 0.3 RPM, at a temperature of 25° C.

It has been found that the pH affects not only viscosity but also stability and appearance. Regarding viscosity, at a pH of below 5.0 and where the composition is a gel, the viscosity is too low and the composition is too fluid to be applied to the glans without being spread or spontaneously dissipating away from the glans. At pH values greater than 5.0, preferably greater than 5.2, viscosity is acceptable although, at a pH above about 5.8, there is an increasing risk, depending on other ingredients present in the composition, that the thickening or gelling agent will form a precipitate, thus rendering the composition visually unacceptable. It has been found that the tendency towards flocculation, arising from or exacerbated by the thickening or gelling agent, is mitigated by the pH. In particular, viscosity is unacceptable at a pH significantly below 5.2 whereas, at a pH greater than 5.8, there is a significant risk of flocculation occurring, resulting in a product which may be regarded by consumers as unacceptable.

Within the broad pH range of 5.0-7.0, a preferred range is 5.2-6 and a more preferred range is 5.25-5.75. At a pH within this range, viscosity and flocculation are acceptable.

The above pH values refer to the composition as manufactured, although there may be a tendency for the pH to drift upwards by up to approximately 0.25 of a pH unit within a few weeks of manufacture. Nevertheless, since higher viscosities can be tolerated, any increase in pH after manufacture is also acceptable.

Because of the tendency for upward drift of pH following manufacture, the more preferred pH range for compositions according to the invention should be regarded as 5.25-6.0 and the upper values of the other ranges should be adjusted accordingly.

Compositions according to the invention may also include, depending on their physical form, at least one additional ingredient selected from: agents for enhancing skin feel, for example a silicone oil composition such as Dimethicone 200; a thickening or gelling agent such as a polyacrylate-based composition; a pH control agent such as triethanolamine or an inorganic base; and an antimicrobial preservative such as methylparaben and/or propylparaben.

Concentrations of the additional ingredients are preferably less than 5% by weight, preferably less than 2% by weight, for example 1.0%. However, the pH control agent is added until the pH is within the desired target range of 5.0-7.0, preferably 5.1-6.0 or more preferably 5.25-5.75, all as manufactured.

Regarding the thickening or gelling agent, it has been found desirable to use a polyacrylate-based composition which is readily dispersible in the solvent blend and which facilitates rapid evaporation of the volatile solvents so as to achieve the equilibrium rate for skin permeation preferably within one minute or more preferably within thirty seconds of application to the penis. Suitable thickening or gelling agents comprise high molecular weight interpolymers of a crosslinked unsaturated carboxylic acid polymer, which may be a homopolymer or a copolymer, and a copolymeric steric stabiliser having hydrophilic and hydrophobic moieties. Preferably, the monomer of the unsaturated carboxylic acid polymer comprises acrylic acid or an alkyl ester derivate thereof, and the steric stabiliser preferably comprises either a block copolymer and/or a random copolymer, the block copolymer preferably comprising a polyester such as 12-hydroxystearic acid as the hydrophobic moiety and polyethylene glycol as the hydrophilic moiety. Preferably, the unsaturated carboxylic acid comprises acrylic acid crosslinked with allyl sucrose. Such interpolymers which include a steric stabiliser in the polymerisation process are rapidly wetted and easy to disperse and, throughout the remainder of this specification, including the claims, will be referred to as "easy to disperse interpolymers of the type described". Commercially-available representative examples include the cross-linked polyacrylic interpolymers CARBOPOL® Ultrez 10, 20, 21 and 30 (Lubrizol Advanced Materials, Inc., Cleveland, OH). Homopolymers such as CARBOPOL® 934P and 937P are not "easy to disperse interpolymers of the type described", since they do not include the steric stabiliser.

The thickening or gelling agent is preferably present in the composition at 0.5% to 2% by weight. In some embodiments, the composition comprises a thickening or gelling agent at 0.5% to 1.5% by weight. In other embodiments, the composition comprises a thickening or gelling agent at 0.7% to 1.5% by weight. In various embodiments, the composition comprises a thickening or gelling agent at 0.8% to 1.2% by weight. In particular embodiments, the composition comprises a thickening or gelling agent at about 1% by weight.

Compositions according to the invention may be considered as a single-phase solution comprising the volatile solvent pair of, for example, ethanol and water and the non-volatile solvent pair of, for example, glycerol and propylene glycol. The use in such systems of a gelling agent comprising an easy to disperse interpolymer of the type described and having the required pH has been found to permit precise application of the composition to the glans penis. Additionally, the use of easy to disperse interpolymers of the type described, especially CARBOPOL® Ultrez 10, surprisingly results in higher viscosities than previously imagined being advantageously acceptable, since such interpolymers of the type described result in the compositions having rheological properties such that, in use and on being applied to the glans of the penis by hand, the rubbing or smearing action results in a temporary reduction in viscosity such that evaporation of volatile solvent is rendered even more rapid, whereby equilibrium is established in the target time of less than one minute, preferably less than 30 seconds. At the same time, permeation is unaffected by the increased viscosity under non-shear conditions.

The volatile solvents may have a molecular weight of 15 to 75 g/mol. The non-volatile solvents may have a molecular weight of 40 to 200 g/mol, preferably 50 to 150 g/mol, and more preferably 60 to 120 g/mol.

The volatile solvents to non-volatile solvents may have a ratio by weight of from 0.5:1 to 4:1. Preferably, the volatile solvent to non-volatile solvent ratio by weight is from 1:1 to 3:1. More preferably, the volatile solvent to non-volatile solvent ratio by weight is from 2:1 to 2.5:1.

The polyhydric alcohol preferably has a carbon to oxygen atom ratio of from 2:1 to 1:1. The glycol preferably has a carbon to oxygen atom ratio of from 2:1 to 1:1.

The lower alcohol preferably has a boiling point below 150° C. The polyhydric alcohol preferably has a boiling point below 150° C. The glycol preferably has a boiling point below 250° C.

Compositions according to the invention may be fully water miscible. The volatile and non-volatile solvents may be water miscible.

Compositions according to the invention may be clear and/or colourless.

Preferably, the polyhydric alcohol and the glycol have a ratio by weight of from 2:1 to 6:1. More preferably, the polyhydric alcohol to glycol ratio by weight is from 2.5:1 to 5.5:1. Even more preferably, the polyhydric alcohol to glycol ratio by weight is from 3:1 to 5:1. More preferably still, the polyhydric alcohol to glycol ratio by weight is from 3.5:1 to 4.5:1.

In terms of concentration of ingredients, compositions according to the invention may comprise the following, the ranges being expressed in percentages by weight of the overall composition:
  lower alcohol: 30-45%
  water: 20-40%
  polyhydric alcohol: 22-26%
  glycol: 4-12%

The concentration of water is preferably in the range 30-40% by weight. The 20% referred to above is the minimum which is preferred for gelling purposes. Likewise, the lower alcohol concentration is preferably in the range 30-35% by weight but, subject to user tolerance, concentrations up to 45% may be accommodated without compromising the efficacy of the composition. The ratio of ethanol to water in the volatile solvent pair may be adjusted to alter the rate of evaporation, ethanol being more volatile than water, up to approximately 1:1, the limiting concentration of ethanol as an example of the lower alcohol being governed by local intolerance as a skin irritant.

Preferably, the combined amount of the polyhydric alcohol and the glycol is not more than 35% by weight.

In the present specification, the term "lower alcohol" means an aliphatic alcohol having from one to five carbon atoms, for example, ethanol or isopropanol; ethanol is generally preferred.

By "polyhydric alcohol" is meant an aliphatic polyol such as glycerol, although sorbitol, erythrotol, arabitol and xylitol are examples of other water-soluble polyols which may optionally be used together with or instead of glycerol.

By "glycol" is meant a primary or secondary diol or polyol compound, such as propylene glycol (propene-1,2-diol), butyline glycol (butane-1,3-diol), pentylene glycol (pentane-1,5-diol) or hexyline glycol (2-methyl-2,4-pentane diol). Preferably, the glycol is a primary or secondary diol.

Preferably, compositions according to the invention have the following concentrations in percentages by weight:
  lower alcohol: 30-35%
  water: 33-37%
  polyhydric alcohol: 22-26%
  glycol: 4-8%

By way of example, one formulation according to the invention has the following ingredients in percentages by weight:
  ethanol: 33%
  water: 35%
  glycerol: 24%
  propylene glycol: 6%

By way of example, another formulation according to the invention has the following ingredients in percentages by weight:
  ethanol: 33%
  water: 35%
  glycerol: 24%
  propylene glycol: 6%
  CARBOPOL® Ultrez 10: 1%

In the above formulations, the ratio of glycerol to propylene glycol is 4:1. The above formulations may also contain a base to bring the pH within the range of 5.0-7.0.

Compositions according to the invention may be made by mixing the ingredients together. Conventional process principles may be applied, for example that the CARBOPOL® Ultrez 10 is dispersed in the water phase, the ethanol added and the remaining solvents then added optionally with or before pH adjustment. While an organic base, such as triethanolamine, may be used for the purpose of pH adjustment, it is preferred to use an inorganic base such as potassium hydroxide, sodium hydroxide or liquid ammonia, to avoid a possibility of nitrosamine formation. Such bases, preferably potassium hydroxide, are especially beneficial in solvent-rich systems such as those according to the present invention, since the potassium, for example, has the potential to form a salt with the gelling agent, the salt possibly being insoluble at the concentrations used, leading to phase separation after manufacture. Easy to disperse interpolymers of the type described appear to be less susceptible to phase separation, due possibly to the increased solvent affinity of the block copolymer backbone segments. Even so, it is considered preferable to control pH to within a range of 5.25 to 5.75 such that precision of application is achieved, CARBOPOL® salt phase separation (e.g. using CARBOPOL® Ultrez 10, 20, 21 or 30) does not occur and gel viscosity does not compromise rate of loss of volatile solvents.

According to a second aspect of the invention, a composition (as herein before described) is provided for use in therapy.

According to a third aspect of the invention, there is provided the composition (as herein before described) for use in treating or ameliorating erectile dysfunction. Also provided is the use of the composition (as herein before described) in the manufacture of a medicament for treating or ameliorating erectile dysfunction.

According to a fourth aspect of the invention, there is provided a method for treating or ameliorating erectile dysfunction, the method comprising topical application of a biologically effective amount of the composition (as herein before described) to the penis, preferably to the glans thereof, of a male subject. Optionally, the method may further comprise manual stimulation of the penis.

The subject may have an existing medical condition, wherein the existence of the condition precludes the taking of an active ingredient for treating erectile dysfunction. The subject may have an existing medical condition, wherein the treatment of the condition precludes the taking of an active ingredient for treating erectile dysfunction, The existing medical condition may be any condition that precludes the taking of an active ingredient for treating erectile dysfunction. For example, the existing medical condition may be angina, low blood pressure, high blood pressure, benign prostatic hyperplasia, or retinitis pigmentosa.

Treatment of the existing medical condition which precludes the taking of an active ingredient for treating erectile dysfunction may involve the administration of an active ingredient selected from PDE-5 inhibitors, nitrates and alpha blockers. For example, the active ingredient for treating the existing medical condition may be selected from GTN, isosorbide mononitrate, isosorbide dinitrate, alfuzosin, doxazosin, indoramin, prazosin, tamsulosin, and terazosin.

The method may further comprise administering at least one active agent for treating or ameliorating erectile dysfunction to the subject, wherein the method excludes the topical application of GTN, sildenafil or an acetylcholinesterase inhibitor to the penis of the subject. The at least one active agent for treating or ameliorating erectile dysfunction may be selected from PDE-5 inhibitors, alprostadil and phentolamine mesilate. In one embodiment, the at least one active agent for treating or ameliorating erectile dysfunction is administered orally.

The male subject may have severe erectile dysfunction.

According to a fifth aspect of the invention, there is provided a condom comprising the composition (as herein before described).

According to a sixth aspect of the invention, there is provided a kit comprising the composition (as herein before described) and an active agent for treating or ameliorating erectile dysfunction, wherein the kit does not comprise GTN, sildenafil or an acetylcholinesterase inhibitor for inclusion in the composition. The active agent is preferably administered separately from the composition, e.g. it is not intended to be added to the topical composition (as herein before described). The active agent may be selected from PDE-5 inhibitors, alprostadil and phentolamine mesilate. In one embodiment, the active agent for treating or ameliorating erectile dysfunction is for oral administration, i.e. it is in an oral dosage form.

According to a seventh aspect of the invention, there is provided a method of determining the cooling ability of a test composition, the method comprising:

applying a layer of the test composition to a temperature probe, wherein the test composition and the temperature probe are at a pre-determined temperature which is between about 25° C. and about 50° C.;

placing the temperature probe in an environment which has a relatively constant temperature which is the same as the pre-determined temperature;

monitoring the temperature change of the temperature probe over time; and optionally monitoring the weight change of the temperature probe over time.

In the applying step of the method, the temperature probe and the test composition are at substantially the same temperature when the layer of the test composition is applied to the temperature probe.

In some embodiments, between about 30 mg and about 120 mg of test composition are applied to the temperature probe. Preferably, between about 40 mg and about 100 mg of test composition are applied to the temperature probe. More preferably, between about 50 mg and about 90 mg of test composition are applied to the temperature probe. Preferably, the test composition is applied to the temperature probe such that the layer of the test composition is of a substantially even thickness.

In various embodiments, the temperature change of the temperature probe, and optionally the weight change of the temperature probe, is monitored for at least about 5 minutes. Preferably, the temperature change of the temperature probe, and optionally the weight change of the temperature probe, is monitored for between about 5 minutes and about 45 minutes. More preferably, the temperature change of the temperature probe, and optionally the weight change of the temperature probe, is monitored for between about 10 minutes and about 40 minutes. More preferably still, the temperature change of the temperature probe, and optionally the weight change of the temperature probe, is monitored for between about 15 minutes and about 35 minutes. Even more preferably, the temperature change of the temperature probe, and optionally the weight change of the temperature probe, is monitored for between about 20 minutes and about 30 minutes. In some embodiments, the temperature change of the temperature probe, and optionally the weight change of the temperature probe, is monitored for about 25 minutes.

In some embodiments, prior to the applying step, the test composition and the temperature probe are incubated in an environment which has a relatively constant temperature and which is at the pre-determined temperature so that the test composition and the temperature probe are at the pre-determined temperature for the applying step.

In various embodiments, the pre-determined temperature may be between about 25° C. and about 40° C. In certain embodiments, the pre-determined temperature may be between about 25° C. and about 30° C. In some embodiments, the pre-determined temperature may be between about 30° C. and about 35° C. In other embodiments, the pre-determined temperature may be between about 35° C. and about 40° C. In particular embodiments, the pre-determined temperature is 27° C.±1° C., 32° C.±1° C. or 37° C.±1° C.

The method is preferably carried out at atmospheric pressure, for example, at about 1 atm or about 100 kPa.

In some embodiments, the method is carried out at a relative humidity of between about 40% and 60%.

In some embodiments, the weight of the temperature probe is measured before the application of the test composition.

In certain embodiments, the method comprises:

incubating the test composition and a temperature probe in an environment which has a relatively constant temperature and which is at a pre-determined temperature between about 25° C. and about 40° C.;

applying a layer of between about 40 mg and about 100 mg of the test composition to the temperature probe, wherein the test composition and the temperature probe are at the pre-determined temperature;

placing the temperature probe in an environment which has a relatively constant temperature and which is at the pre-determined temperature; and monitoring the temperature change and the weight change of the temperature probe for between about 20 minutes and about 30 minutes.

In a particular embodiment, there is provided a method of determining the cooling ability of a test composition, the method comprising the following steps:

1. Drill a hole about 5 mm in diameter into a 15 mL centrifuge tube lid. Weigh the empty centrifuge tube on an analytical balance.

2. Place about 14 mL of sample gel into the 15 mL centrifuge tube. Seal with a normal lid and centrifuge at about 1500 rpm for about 30 seconds to collect the gel.

3. Place the tube containing sample gel, a calibrated temperature probe and an analytical balance into a bench top oven set at 32° C.±1° C.

4. Weigh the tube containing the sample gel. (Weight Check 1).

5. Leave all apparatus including the tube containing sample gel overnight to incubate.

6. After incubation, weigh the tube containing the sample gel. (Weight Check 2).

7. Place the lid with the 5 mm hole cut out onto the centrifuge tube containing sample gel. Stopper the hole to prevent any evaporation until it is ready to be sampled. Place back into the benchtop oven.

8. Tare the balance with the temperature probe. Ensure the temperature of the probe is within 32° C.±1° C.

9. Remove the temperature probe from the balance and insert it into centrifuge tube containing sample gel until the base of the probe makes contact with the tube lid. Approximately 70 mg is applied (±20 mg). (NB: Time sensitive step).

10. In one smooth motion, withdraw the probe from the gel taking care not to make contact with the sides of the centrifuge cap. Place the probe back onto the balance, close the oven door and start the stopwatch. (NB: Time sensitive step).

11. Record the weight and temperature of the probe for 25 minutes.

The above method can alternatively be carried out at a temperature of 27° C.±1° C. or 37° C.±1° C.

The invention also provides a composition which provides a maximum temperature reduction of at least 5° C. when tested using the method described above. The maximum temperature reduction is calculated by subtracting the lowest temperature reached by the temperature probe (° C.) from the pre-determined temperature (° C.) (also referred to as the ambient temperature in the detailed description hereinafter). The composition may provide a maximum temperature reduction of at least 6° C. when tested using the method described above. The composition may provide a maximum temperature reduction of at least 7° C. The composition may provide a maximum temperature reduction of at least 8° C. The composition may provide a maximum temperature reduction of at least 9° C. The composition may provide a maximum temperature reduction of at least 10° C. The composition may provide a maximum temperature reduction of at least 11° C.

In some embodiments, the composition provides a maximum temperature reduction of between about 5° C. and about 15° C. when tested using the method described above. The composition may provide a maximum temperature reduction of between about 6° C. and about 15° C. The composition may provide a maximum temperature reduction of between about 7° C. and about 15° C. The composition may provide a maximum temperature reduction of between about 8° C. and about 14° C. The composition may provide a maximum temperature reduction of between about 9° C. and about 13° C. The composition may provide a maximum temperature reduction of between about 10° C. and about 12° C.

In various embodiments, the composition provides a maximum temperature reduction of at most 15° C. when tested using the method described above. The composition may provide a maximum temperature reduction of at most 14° C. The composition may provide a maximum temperature reduction of at most 13° C. The composition may provide a maximum temperature reduction of at most 12° C.

In some embodiments, the composition provides a temperature reduction after 1 minute of monitoring of at least 5° C. when tested using the method described above. The temperature reduction is calculated by subtracting the temperature reached after 1 minute of monitoring (° C.) from the pre-determined temperature (° C.). The composition may provide a temperature reduction after 1 minute of monitoring of at least 6° C. when tested using the method described above. The composition may provide a temperature reduction after 1 minute of monitoring of at least 7° C. The composition may provide a temperature reduction after 1 minute of monitoring of at least 8° C. The composition may provide a temperature reduction after 1 minute of monitoring of at least 9° C. The composition may provide a temperature reduction after 1 minute of monitoring of at least 10° C. The composition may provide a temperature reduction after 1 minute of monitoring of at least 11° C.

In some embodiments, the composition provides a temperature reduction after 1 minute of monitoring of between about 5° C. and about 15° C. when tested using the method described above. The composition may provide a temperature reduction after 1 minute of monitoring of between about 6° C. and about 15° C. The composition may provide a temperature reduction after 1 minute of monitoring of between about 7° C. and about 15° C. The composition may provide a temperature reduction after 1 minute of monitoring of between about 8° C. and about 14° C. The composition may provide a temperature reduction after 1 minute of monitoring of between about 9° C. and about 13° C. The composition may provide a temperature reduction after 1 minute of monitoring of between about 10° C. and about 12° C.

In some embodiments, the composition provides a temperature recovery after 25 minutes of monitoring of at least 4° C. when tested using the method described above. The temperature recovery is calculated by subtracting the lowest temperature reached by the temperature probe (° C.) from the temperature of the temperature probe (° C.) after 25 minutes of monitoring. The composition may provide a temperature recovery after 25 minute of monitoring of at least 5° C. when tested using the method described above. The composition may provide a temperature recovery after 25 minute of monitoring of at least 6° C. The composition may provide a temperature recovery after 25 minute of monitoring of at least 7° C. The composition may provide a temperature recovery after 25 minute of monitoring of at least 8° C.

In some embodiments, the composition provides a temperature recovery after 25 minutes of monitoring of between about 4° C. and about 15° C. when tested using the method described above. The composition may provide a temperature recovery after 25 minutes of monitoring of between about 4° C. and about 14° C. The composition may provide a temperature recovery after 25 minutes of monitoring of between about 4° C. and about 13° C. The composition may provide a temperature recovery after 25 minutes of monitoring of between about 4° C. and about 12° C. The composition may provide a temperature recovery after 25 minutes of monitoring of between about 5° C. and about 11° C. The composition may provide a temperature recovery after 25 minutes of monitoring of between about 6° C. and about 10° C. The composition may provide a temperature recovery after 25 minutes of monitoring of between about 7° C. and about 9° C.

In particular embodiments, when the composition is tested at a pre-determined temperature of 32° C.±1° C.,
 1) the composition provides a maximum temperature reduction of at least 9° C.;
 2) the composition provides a maximum temperature reduction of between about 9° C. and about 13° C.;
 3) the composition provides a temperature reduction after 1 minute of monitoring of at least 9° C.;
 4) the composition provides a temperature reduction after 1 minute of monitoring of between about 9° C. and about 13° C.;
 5) the composition provides a temperature recovery after 25 minute of monitoring of at least 6° C.; and/or
 6) the composition provides a temperature recovery after 25 minute of monitoring of between about 6° C. and about 10° C.

In certain embodiments, the weight change of the composition after 1 minute of monitoring is at least −10% when tested using the method described above. The percentage weight change is calculated as follows: % weight change= −100+((Reading Interval Weight (g)/Initial Weight (g))*100). The weight change of the composition after 1 minute of monitoring may be at least −12%. The weight change of the composition after 1 minute of monitoring may be at least −14%. The weight change of the composition after 1 minute of monitoring may be at least −15%. The weight change of the composition after 1 minute of monitoring may be at least −16%. The weight change of the composition after 1 minute of monitoring may be at least −17%. The weight change of the composition after 1 minute of monitoring may be at least −18%.

In some embodiments, the weight change of the composition after 1 minute of monitoring may be between about −10% and about −30% when tested using the method described above. The weight change of the composition after 1 minute of monitoring may be between about −12% and about −28%. The weight change of the composition after 1 minute of monitoring may be between about −14% and about −26%. The weight change of the composition after 1 minute of monitoring may be between about −15% and about −25%. The weight change of the composition after 1 minute of monitoring may be between about −16% and about −24%. The weight change of the composition after 1 minute of monitoring may be between about −17% and about −23%. The weight change of the composition after 1 minute of monitoring may be between about −18% and about −22%.

In certain embodiments, the weight change of the composition after 5 minutes of monitoring is at least −20% when tested using the method described above. The weight change of the composition after 5 minutes of monitoring may be at least −25%. The weight change of the composition after 5 minutes of monitoring may be at least −30%. The weight change of the composition after 5 minutes of monitoring may be at least −32%. The weight change of the composition after 5 minutes of monitoring may be at least −34%. The weight change of the composition after 5 minutes of monitoring may be at least −35%. The weight change of the composition after 5 minutes of monitoring may be at least −36%. The weight change of the composition after 5 minutes of monitoring may be at least −37%. The weight change of the composition after 5 minutes of monitoring may be at least −38%.

In some embodiments, the weight change of the composition after 5 minutes of monitoring may be between about −20% and about −60% when tested using the method described above. The weight change of the composition after 5 minutes of monitoring may be between about −25% and about −55%. The weight change of the composition after 5 minutes of monitoring may be between about −30% and about −50%. The weight change of the composition after 5 minutes of monitoring may be between about −32% and about −48%. The weight change of the composition after 5 minutes of monitoring may be between about −34% and about −46%. The weight change of the composition after 5 minutes of monitoring may be between about −35% and about −45%. The weight change of the composition after 5 minutes of monitoring may be between about −36% and about −44%.

In certain embodiments, the weight change of the composition after 25 minutes of monitoring is at least −40% when tested using the method described above. The weight change of the composition after 25 minutes of monitoring may be at least −45%. The weight change of the composition after 25 minutes of monitoring may be at least −50%. The weight change of the composition after 25 minutes of monitoring may be at least −52%. The weight change of the composition after 25 minutes of monitoring may be at least −54%. The weight change of the composition after 25 minutes of monitoring may be at least −55%. The weight change of the composition after 25 minutes of monitoring may be at least −56%. The weight change of the composition after 25 minutes of monitoring may be at least −57%. The weight change of the composition after 25 minutes of monitoring may be at least −58%. The weight change of the composition after 25 minutes of monitoring may be at least −59%. The weight change of the composition after 25 minutes of monitoring may be at least −60%.

In some embodiments, the weight change of the composition after 25 minutes of monitoring may be between about −40% and about −90% when tested using the method described above. The weight change of the composition after 25 minutes of monitoring may be between about −45% and about −85%. The weight change of the composition after 25 minutes of monitoring may be between about −50% and about −80%. The weight change of the composition after 25 minutes of monitoring may be between about −52% and about −78%. The weight change of the composition after 25 minutes of monitoring may be between about −54% and about −76%. The weight change of the composition after 25 minutes of monitoring may be between about −55% and about −75%. The weight change of the composition after 25 minutes of monitoring may be between about −56% and about −74%. The weight change of the composition after 25 minutes of monitoring may be between about −57% and about −73%. The weight change of the composition after 25 minutes of monitoring may be between about −58% and about −72%. The weight change of the composition after 25 minutes of monitoring may be between about −59% and about −71%. The weight change of the composition after 25 minutes of monitoring may be between about −60% and about −70%.

In certain embodiments, the weight change of the composition when the maximum temperature reduction is reached is at least −10% when tested using the method described above. The weight change of the composition when the maximum temperature reduction is reached may be at least −12%. The weight change of the composition when the maximum temperature reduction is reached may be at least −14%. The weight change of the composition when the maximum temperature reduction is reached may be at least −15%. The weight change of the composition when the maximum temperature reduction is reached may be at least −16%. The weight change of the composition when the maximum temperature reduction is reached may be at least −17%. The weight change of the composition when the maximum temperature reduction is reached may be at least −18%.

In some embodiments, the weight change of the composition when the maximum temperature reduction is reached is between about −10% and about −35% when tested using the method described above. The weight change of the composition when the maximum temperature reduction is reached may be at between about −12% and about −33%. The weight change of the composition when the maximum temperature reduction is reached may be at between about −14% and about −31%. The weight change of the composition when the maximum temperature reduction is reached may be at between about −15% and about −30%. The weight change of the composition when the maximum temperature reduction is reached may be at between about −16% and about −29%. The weight change of the composition when the maximum temperature reduction is reached may be at between about −17% and about −28%. The weight change of the composition when the maximum temperature reduction is reached may be at between about −18% and about −27%. The weight change of the composition when the maximum temperature reduction is reached may be at between about −18% and about −26%. The weight change of the composition when the maximum temperature reduction is reached may be at between about −18% and about −25%.

In a particular embodiment, the weight change of the composition when the maximum temperature reduction is reached is between about −15% and about −25%.

In the embodiments described above relating to the weight change of the composition, the composition may be tested at a pre-determined temperature of 32° C.±1° C.

In some embodiments, the rate of cooling provided by the composition in the temperature reduction phase is faster than the rate of warming provided by the composition in the temperature recovery phase.

In some embodiments, the rate of cooling provided by the composition in the temperature reduction phase is faster when the composition is tested at a higher pre-determined temperature.

In various embodiments, the rate of cooling provided by the composition in the temperature reduction phase is substantially proportional to the rate of weight loss of the composition in the temperature reduction phase.

BRIEF DESCRIPTION OF THE DRAWINGS

The invention will now be described in detail by way of example only with reference to the figures in which.

DETAILED DESCRIPTION OF THE INVENTION

Efficacy of Composition

Figure 1:
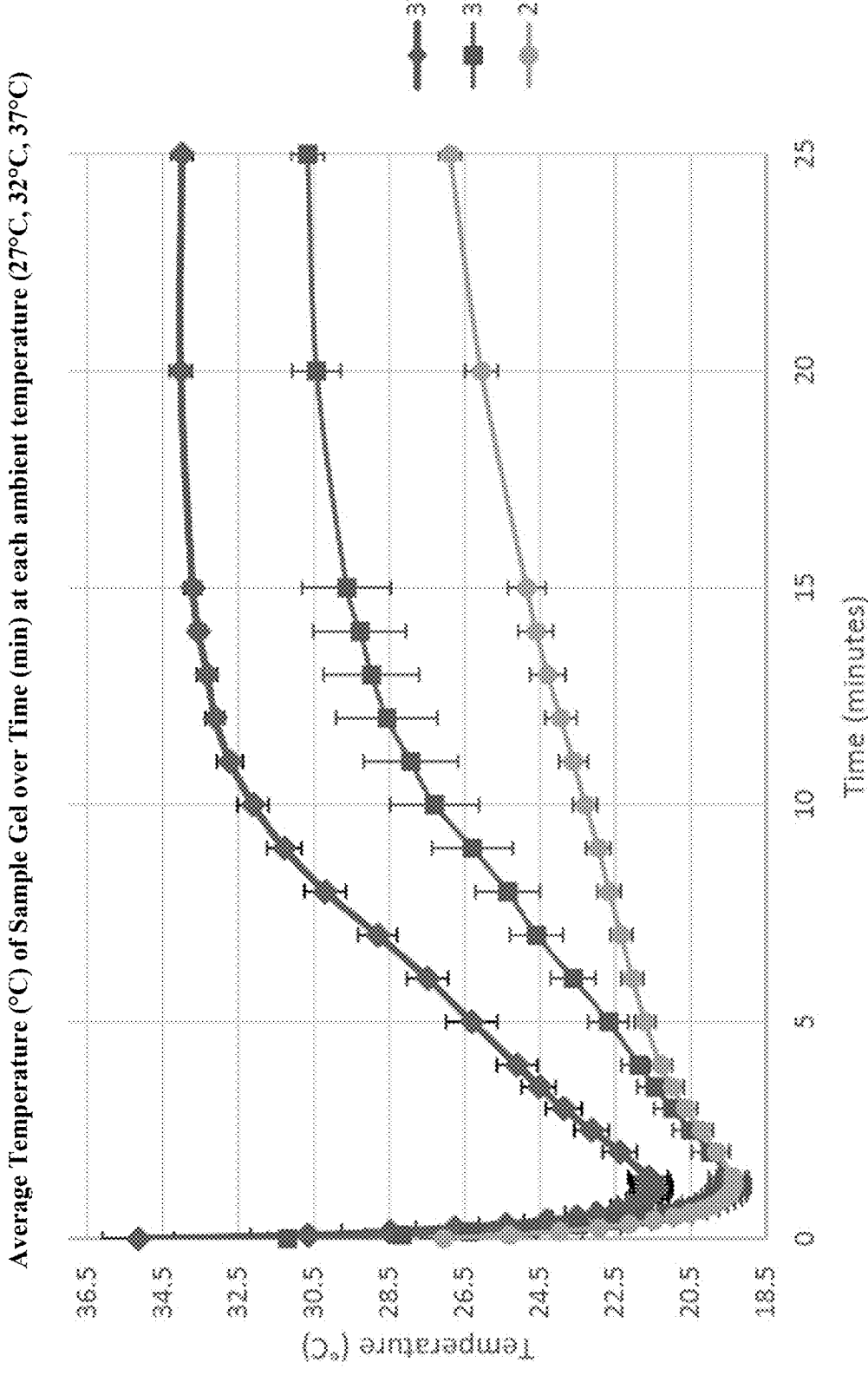
FIG. 1 is a graph showing the average temperature (° C.) of the sample gel over time (min) at each ambient temperature (27° C., 32° C., 37° C.).

The results of a clinical trial of compositions according to the invention show that they are equivalent in performance to compositions containing GTN as active ingredient, as set out hereinbefore. The composition of the invention contained: ethanol: 33%; water: 35%; glycerol: 24%; propylene glycol: 6%; CARBOPOL® Ultrez 10: 1%. pH was adjusted to 5.25 with potassium hydroxide solution. The ethanol used in the manufacture of the composition was absolute ethanol (i.e. 100% ethanol free from water) such that the final composition contained 33% of pure ethanol. If a lower grade of ethanol was used which contained impurity amounts of water (e.g. 96% ethanol), then the amount used would have to be adjusted to ensure the final composition contained the correct amount of the components, i.e. 33% pure ethanol and 35% water.

The availability of an efficacious composition for treatment of erectile dysfunction, without the inclusion of GTN or any other active ingredient, means that the composition has reduced contraindications compared with other treatments, thus for example enabling the composition to be used by men taking nitrate medication. Furthermore, the high safety profile enables the compositions to be used in conjunction with other treatments such as sildenafil. In summary, compositions according to the invention, in providing fast onset time and sustained erection quality, together with a high safety profile, represent a significant improvement to known treatments and offer further treatment opportunities to patients who hitherto have been unable to or are contraindicated to use currently-available treatments.

The appended Tables show clinical trial results for compositions according to the invention, compared with equivalent compositions containing GTN and with commercially-available Cialis and Vitaros. In the results, the IIEF figures are on the basis of questionnaire responses relating to the evaluation of male sexual function and SWEP2 and SEP3 respectively relate to the ability to insert the penis into the vagina and the ability of the erection to sustain long enough for completion of intercourse.

Primary Endpoints at 12 Weeks vs Baseline

| Primary Endpoint | Invention | P-values | 0.6 mg (0.2%) GTN | P-values | 1.2 mg (0.4%) GTN | P-values | 1.8 mg (0.6%) GTN | P-values |
|---|---|---|---|---|---|---|---|---|
| IIEF-EF Domain | 3.60 | <0.001 | 3.39% | <0.001 | 3.42% | <0.001 | 3.66% | <0.001 |
| SEP2 | 13.8% | <0.001 | 9% | <0.001 | 13.27% | <0.001 | 10.67% | <0.001 |
| SEP3 | 23.16% | <0.001 | 20.76% | <0.001 | 22.63% | <0.001 | 23.27% | <0.001 |

Clinically Important Differences at 12 Weeks (Rosen & Araujo)—Percentage of Patients Who Noticed a Meaningful Difference

| Invention | Overall responders using Rosen/Araujo (%) | Responders in patients with Mild/Moderate/Severe ED using Rosen/Araujo (%) |
|---|---|---|
| IIEF | 63 | 61/59/80 |
| SEP2 | 75 | 83/57/77 |
| SEP3 | 68 | 71/61/71 |

Primary Endpoints vs Baseline for Composition of the Invention, Cialis & Vitaros

| Primary Efficacy Parameters | Invention | Cialis 5 mg | Vitaros 100, 200 & 300 ug |
|---|---|---|---|
| IIEF | 3.6 | 4.6 | 1.6/2.5/2.4 |
| SEP2 | 13.8% | 16.5% | 2.9%/5.1%/7.2% |
| SEP3 | 23.2% | 21.5% | 7.0%/13.8%/9.1% |

Side Effect Profile—Invention vs. Cialis

| Adverse events - Invention | Invention (N = 250) | Adverse events - Cialis | Cialis 5 mg (N = 151) |
|---|---|---|---|
| Headache | 3% | Headache | 11% |
| Flushing | 0% | Flushing | 2% |
| Nasal congestion | 0% | Nasal congestion | 2% |
| Back pain | 0% | Back pain | 3% |
| Dizziness | 0% | Myalgia | 2% |
| Penile burning | 1% | Pain in limb | 1% |

Cooling Effect of Composition

As indicated above, the compositions of the invention are believed to enhance production of endogenous NO by virtue of the latent heat of cooling as the volatile solvent component evaporates, stimulating the nerves locally and resulting in generation of endogenous NO. In the glans of the penis, there are sensors which are reactive to a range of physical sensations, such as and including touch, pressure and temperature, and topical application of compositions of the invention stimulate such sensors. It is thought that the rapid cooling brought about by the composition followed by the recovery in temperature acts as a stimulant so that the sensors react synergistically and result in tumescence and erection without the inclusion of an active ingredient.

The cooling effect of the composition used in the clinical trial above (ethanol: 33%; water: 35%; glycerol: 24%; propylene glycol: 6%; CARBOPOL® Ultrez 10: 1%. pH adjusted to 5.25 with potassium hydroxide solution) was tested and a protocol developed to enable the comparison of the cooling effect of different compositions.

1. Principle

The cooling effect and rate of recovery of the gel composition is measured by applying the gel to a calibrated temperature probe that is weighed on an analytical balance. This allows the temperature change to be monitored simultaneously with weight loss over time. Different cooling/recovery 'profiles' can be generated when incubating the setup at different ambient temperatures (i.e. 27° C., 32° C. and 37° C.).

2. Summary

A suitable method to assess the cooling profiles of the composition of the invention was developed at three different ambient temperatures: 27° C., 32° C. and 37° C. The method was issued to describe the process used to obtain the cooling profiles.

The results of the validation studies confirm that the method is fit for purpose regarding the repeatability (precision), reproducibility (intermediate precision) and accuracy.

3. Instruments & Apparatus

Temperature probe (e.g. Fisherbrand Traceable Flip-Stick Thermometer, P/N: 14-648-45). Total probe surface area: 11.64 $cm^2$ 15 mL plastic centrifuge tubes or equivalent Power drill capable of drilling a 5 mm diameter hole or equivalent Analytical balance (e.g. Sartorius 4 decimal place Analytical Balance or equivalent)

Stopwatch

Bench top oven capable of maintaining 27° C., 32° C. and 37° C.±1° C.

Bench top centrifuge

Video recorder/Camera

4. Sample

The following sample was used for the validation:

Gel comprising ethanol: 33%; water: 35%; glycerol: 24%; propylene glycol: 6%; CARBOPOL® Ultrez 10: 1%. pH adjusted to 5.25 with potassium hydroxide solution.

5. Method Development

Development of the method utilised three different ambient temperatures: 27° C., 32° C. and 37° C., to assess the cooling profile of the sample gel. A description of the method can be found in section 6 (32° C. described only). The temperature and weight of the gel was recorded over a run time of 25 minutes. Six replicate preparations were performed and the average of the data calculated at each ambient temperature. The following cooling profiles were generated: Temperature vs Time (FIG. 1), % Weight Change vs Time (FIG. 2) and % Weight Change vs Temperature (FIG. 3). It is intended that these cooling profiles can be used to uniquely characterise the cooling properties of the sample gel.

During development, it was observed that the first replicate on each day at each ambient temperature was further from the mean result when compared to the other five replicates of data. This could be caused by fluctuations in oven temperature when opening the oven door for the first time after overnight incubation. For this reason, it was decided for the validation studies to disregard the first replicate on each day in order to allow the oven to stabilise before further replicates were performed.

The results obtained for the development work show that a different cooling profile is achieved when analysing at different ambient temperatures. This difference in the cooling profile is most apparent when plotting Temperature (° C.) against Time (minutes) (FIG. 1). At all three ambient temperatures, the temperature of the gel reached the lowest point after ~1-1.5 minutes and then began to recover back to the ambient temperature. The temperature drop appeared to increase as the ambient temperature increased with an ambient temperature of 37° C. showing a temperature drop of ~13° C. compared to ~8° C. at an ambient temperature of 27° C. After 25 minutes, the sample gel had recovered to within ~3° C. of the initial starting temperature (ambient). The plateau of the temperature recovery occurred at ~15 minutes for 37° C. ambient and at 32° C. and 27° C., both levelled off at ~25 minutes.

Figure 2:
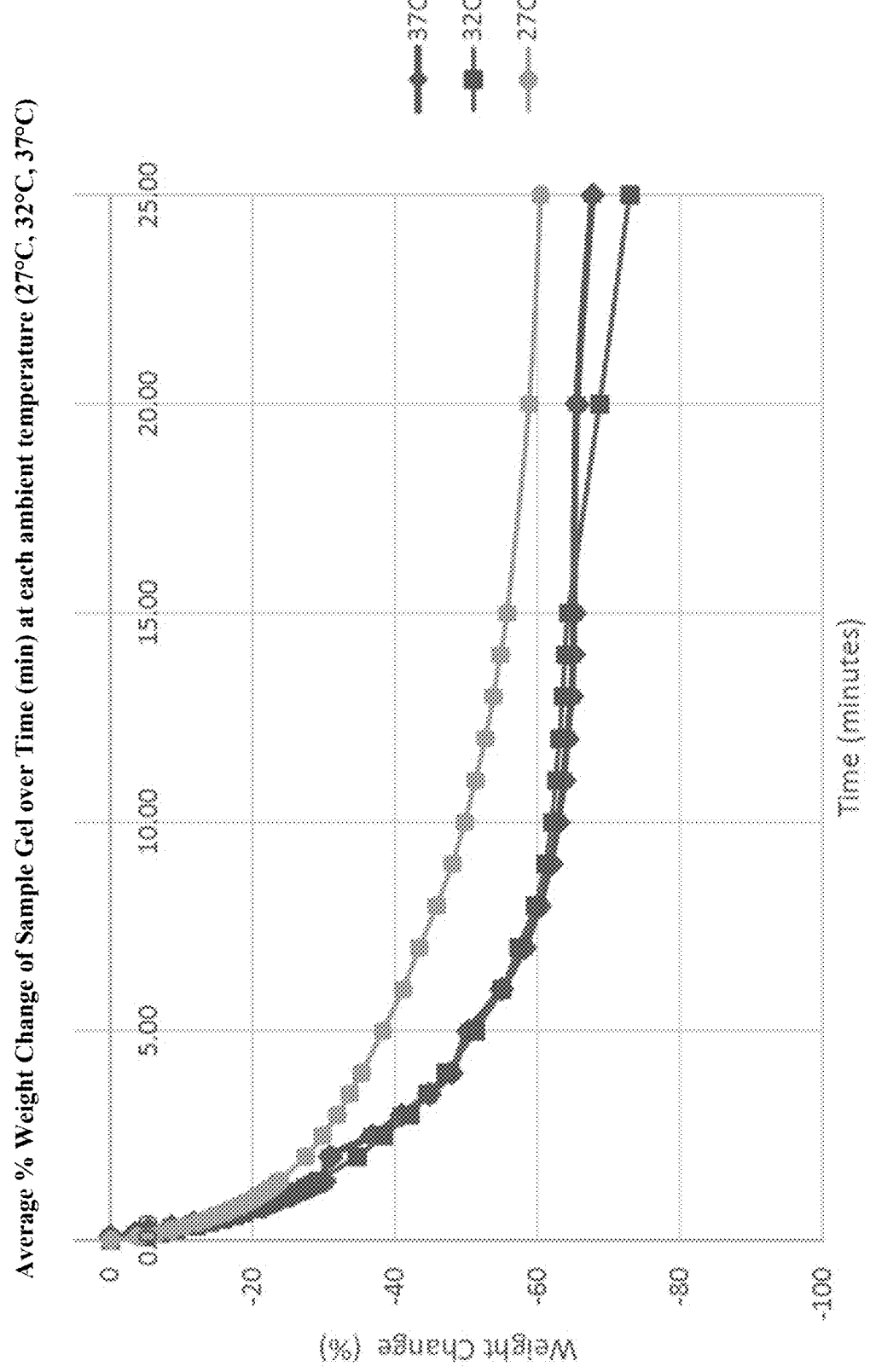
FIG. 2 is a graph showing the average % weight change of the sample gel over time (min) at each ambient temperature (27° C., 32° C., 37° C.).
Figure 3:
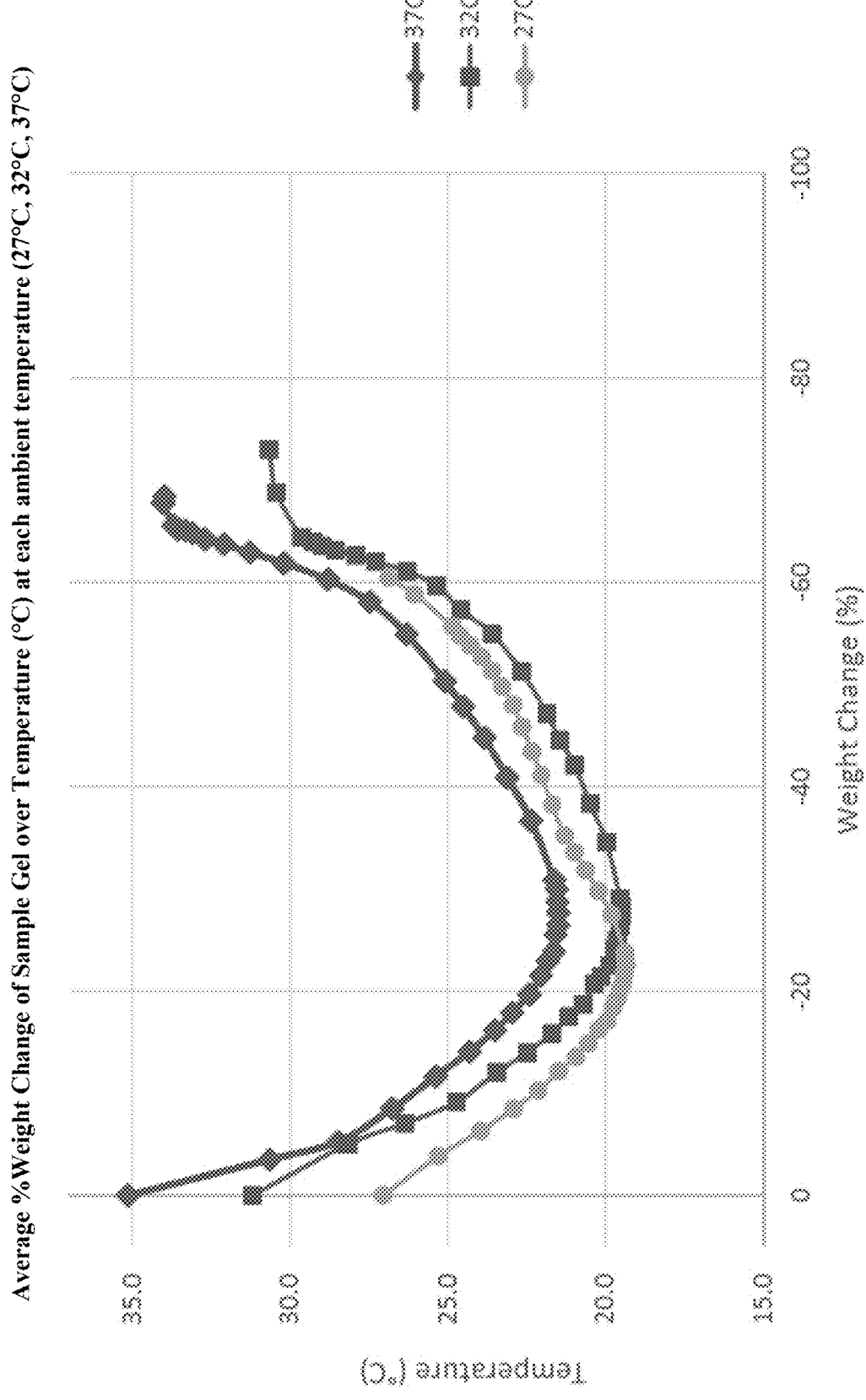
FIG. 3 is a graph showing the average % weight change of the sample gel over temperature (° C.) at each ambient temperature (27° C., 32° C., 37° C.).

FIG. 2 shows the cooling profiles at each ambient temperature when plotting % Weight Change against Time (minutes). In general, the % weight change is most rapid at the beginning of the curve for all three ambient temperatures where after ~5 minutes the % weight change begins to level off. A second % weight change drop was observed at ~15 minutes for 32° C. and at ~20 minutes for the 37° C. ambient temperature. Overall, a clear difference between the 27° C. and 32° C./37° C. profiles can be seen with the 32° C. profile only showing subtle differences when compared to the 37° C. profile.

The cooling profiles obtained by plotting Temperature (° C.) against % Weight Change are shown in FIG. 3. Again, a similar profile shape was obtained at each of the ambient temperatures. Overall, the shape of these profiles represent a 'U' shape. As the ambient temperature increases, the amount of temperature drop/recovery is also increased as seen in FIG. 1. At ~24% weight change the maximum temperature drop is achieved for all three ambient temperatures. Full temperature recovery requires ~70% weight change for 32° C. and 37° C., whereas only 60% weight change is needed to return to 27° C. ambient.

6. Analytical Guidance

The following steps were carried out to test the sample gel.

Note: the first run on each day of analysis is to be disregarded and treated as a mock run to allow the oven setup to stabilise after the first run.

1. Drill a hole ~5 mm in diameter into a 15 mL centrifuge tube lid. Weigh the empty centrifuge tube on an analytical balance. Record the weight and tare the balance.
2. Place ~14 mL of sample gel into the 15 mL centrifuge tube using a syringe. Seal with a normal lid and centrifuge at 1500 rpm for 30 seconds to collect the gel.

3. Place the tube containing sample gel, a calibrated temperature probe and an analytical balance into a bench top oven set at 32° C.±1° C.
4. Weigh the tube containing the sample gel. Record the weight of the gel (Weight Check 1).
5. Place another calibrated temperature probe inside the balance chamber (for ambient temperature monitoring only). Leave all apparatus including the tube containing sample gel overnight to incubate.
6. After incubation, weigh the tube containing the sample gel. (Weight Check 2). Calculate the weight change and check there is no significant weight loss (NMT 2%).
7. Place the lid with the 5 mm hole cut out onto the centrifuge tube containing sample gel. Stopper the hole to prevent any evaporation until it is ready to be sampled. Place back into the benchtop oven.
8. Tare the balance with the temperature probe. Ensure the temperature of the probe is within 32° C.±1° C.
9. Begin video recording ensuring the temperature and weight are visible. (NB: it is not required to video record beyond 5 minutes. Readings after this time may be manually recorded).
10. Remove the temperature probe from the balance and insert it into centrifuge tube containing sample gel until the base of the probe makes contact with the tube lid. Approximately 70 mg is applied (±20 mg). (NB: Time sensitive step).
11. In one smooth motion, withdraw the probe from the gel taking care not to make contact with the sides of the centrifuge cap. Place the probe back onto the balance, close the oven door and start the stopwatch. Stopper the centrifuge tube lid and centrifuge the tube for 15 seconds at 1500 rpm to collect the gel. Seal the tube with a regular lid and place back into the oven. (NB: Time sensitive step).
12. Record the weight and temperature of the probe for 25 minutes. See Table 2 for reading intervals.
13. If ambient temperature drift is observed, the oven may be maintained at 32° C.±1° C. by adjusting the oven control dial or by venting with a small gap in the oven door on the opposite side of the balance.
14. After 25 minutes, remove the temperature probe from the balance and clean with a dry lint-free tissue. Place the temperature probe back onto the balance maintained at 32° C.±1° C. Repeat steps 7-14 for the next replicate.
15. Repeat all steps for the remaining ambient temperatures of 27° C.±1° C. and 37° C.±1° C.

| Reading Intervals | |
|---|---|
| Time (mins) | Reading Interval |
| 0-1.5 | Every 5 seconds |
| 1.5-4 | Every 30 seconds |
| 4-15 | Every 1 minute |
| 15-25 | Every 5 minutes |

7. Results

Calculate % weight change at each reading interval using the following equation:

$$\% \text{ weight change} = -100 + \big(\big(\text{Reading Interval Weight}\,(g)/\text{Initial Weight}\,(g)\big) * 100\big)$$

Calculate the following:

$$\text{Maximum Temperature Reduction} = \text{Ambient Temperature}\,(^\circ C.) - \text{Lowest Temperature}(^\circ C.)$$

$$\text{Temperature Recovery}\,(T = 25 \text{ mins}) = \text{Final Temperature}\,(^\circ C.) - \text{Lowest Temperature}\,(^\circ C.)$$

In a validation study conducted at an ambient temperature of 32° C.±1° C. in accordance with the protocol given in section 6, the test sample gave the following results:

| Parameter (° C.) | Mean | SD | % RSD | Target Precision (% RSD) |
|---|---|---|---|---|
| Temperature Drop After 1 min | 11.5 | 0.1 | 0.7 | ≤7.5% RSD |
| Maximum Temperature Drop | 11.5 | 0.1 | 1.0 | |
| Temperature Recovery After 25 min | 8.9 | 0.4 | 5.0 | |

The invention claimed is:

1. A composition for topical application to the penis for the treatment of erectile dysfunction, the composition comprising volatile and non-volatile solvents, the volatile solvents comprising a lower alcohol and water and the non-volatile solvents comprising a polyhydric alcohol and a glycol, wherein the composition comprises the following amount of ingredients, the ranges being expressed in percentages by weight of the overall composition:

lower alcohol: 30-35% water: 33-37% polyhydric alcohol: 22-26% glycol: 4-8% a thickening or gelling agent: 0.5-1.5% wherein the thickening or gelling agent comprises high molecular weight interpolymers of a crosslinked unsaturated carboxylic acid polymer, which may be a homopolymer or a copolymer, and a copolymeric steric stabiliser having hydrophilic and hydrophobic moieties, and wherein the composition does not contain any additional components which are pharmaceutically active ingredients.

2. A composition according to claim 1, wherein the monomer of the unsaturated carboxylic acid polymer comprises acrylic acid or an alkyl ester derivate thereof.

3. A composition according to claim 1, wherein the composition has a pH above 5.0 and lower than 7.0.

4. A composition according to claim 1, having the form of a gel.

5. A composition according to claim 4, wherein the composition has the form of a gel having a viscosity in the range 125,000 to 600,000 mPas.

6. A composition according to claim 1, wherein the lower alcohol is ethanol or isopropanol.

7. A composition according to claim 1, wherein the polyhydric alcohol is selected from glycerol, sorbitol, erythritol, arabitol and xylitol.

8. A composition according to claim 1, wherein the glycol is selected from propylene glycol, butylene glycol, pentylene glycol and hexylene glycol.

9. A composition according to claim 1, wherein the polyhydric alcohol to glycol weight ratio is from 1.5:1 to 6.0:1.

10. A composition according to claim 1, wherein the polyhydric alcohol to glycol weight ratio is from 3:1 to 5:1.

11. A composition for topical application to the penis for the treatment of erectile dysfunction, the composition comprising volatile and non-volatile solvents, the volatile solvents comprising a lower alcohol and water and the non-volatile solvents comprising a polyhydric alcohol and a glycol, wherein the composition comprises the following amount of ingredients, the ranges being expressed in percentages by weight of the overall composition:

lower alcohol: 30-35% water: 33-37% polyhydric alcohol: 22-26% glycol: 4-8% a thickening or gelling agent: 0.5-1.5%, wherein the thickening or gelling agent comprises high molecular weight interpolymers of a crosslinked unsaturated carboxylic acid polymer, which may be a homopolymer or a copolymer, and a copolymeric steric stabiliser having hydrophilic and hydrophobic moieties, wherein the composition is in the form of a gel and has a pH as manufactured in the range 5.25 to 5.75, and wherein the composition does not contain any additional components which are pharmaceutically active ingredients.

* * * * *